United States Patent [19]
Herweck et al.

[11] Patent Number: 5,380,314
[45] Date of Patent: Jan. 10, 1995

[54] IN-LINE FLUID RECOVERY SYSTEM

[75] Inventors: Steve A. Herweck, Nashua; Theodore Karwoski, Hollis, both of N.H.

[73] Assignee: Atrium Medical Corporation, N.H.

[21] Appl. No.: 755,032

[22] Filed: Sep. 4, 1991

[51] Int. Cl.6 ............................................. A61M 1/00
[52] U.S. Cl. ...................................... 604/403; 604/4; 604/406; 604/317
[58] Field of Search ................................ 604/4–6, 604/317–321, 403, 406, 408, 133

[56] References Cited

U.S. PATENT DOCUMENTS

| | | | |
|---|---|---|---|
| 3,866,608 | 2/1975 | Reynolds et al. | 128/276 |
| 4,006,745 | 2/1977 | Sorenson et al. | 604/4 |
| 4,033,345 | 7/1977 | Sorenson et al. | 128/214 |
| 4,402,687 | 9/1983 | Denty et al. | 604/319 |
| 4,429,693 | 2/1984 | Blake et al. | 604/133 |
| 4,443,220 | 4/1984 | Hauer et al. | 604/319 |
| 4,445,884 | 5/1984 | Kurtz et al. | 604/4 |
| 4,781,707 | 11/1988 | Boehringer | 604/317 |
| 4,838,872 | 6/1989 | Sherlock | 604/319 |
| 4,846,800 | 7/1989 | Ouriel et al. | 604/4 |
| 4,857,042 | 8/1989 | Schneider | 604/4 |
| 4,981,474 | 1/1991 | Bopp et al. | 604/319 |
| 4,988,342 | 1/1991 | Herweck et al. | 604/321 |

OTHER PUBLICATIONS

Fenwal Laboratories product brochure "Fenwal answers your filtration needs with 80 Micron Filter Sets".
Cosgrove et al. "An Improved Technique for Autotransfusion of Shed Mediastinal Blood".
Sorenson Research "Receptaseal" product literature.
Schaff et al. "Autotransfusion of Shed Mediastinal Blood After Cardiac Surgery".

Primary Examiner—Sam Rimell
Attorney, Agent, or Firm—Lahive & Cockfield

[57] ABSTRACT

Apparatus for blood collection includes a collection bag with a suction inlet, a fluid inlet, and an outlet, and an internal stent that resiliently biases the bag into a fixed shape while moving to modulate abrupt variations in suction level. A gross filter about the outlet is located out of the suction path, eliminating blood damage from drying or cell trauma. Different graduation scales show the true volume of collected fluid under suction conditions during collection and with no suction during reinfusion. Two quick-connects allow in-line connection with a chest drain to provide suction, and mate with each other to close the inlets when the filtered bag is removed for gravity reinfusion. When multiple units are piggy-backed, they fill sequentially and may be removed for reinfusion quickly, with only a single tube reconnection required during surgery.

18 Claims, 4 Drawing Sheets

IN-LINE FLUID RECOVERY SYSTEM

TECHNICAL FIELD

The present invention relates to blood collection systems, and particularly to collection systems wherein a first vessel or assembly includes a suction regulator that produces a continuing draw of suction at a level suitable for wound drainage, and a second vessel is attached between the first vessel and a patient wound drainage tube to collect blood.

A number of devices of this type have been implemented wherein the two vessels are formed as interconnected subchambers of a single, multi-chamber assembly, as described, for example, in applicant's previously-issued U.S. Pat. No. 4,988,342. Another system of this type has employed a collection chamber in the form of a separate flexible bag which fastens to an external stent or frame to function as a collection vessel, and, once filled, is removed from the frame to serve as an infusion bag. Other systems of this overall type have involved early variations of basic "two-bottle" or "three-bottle" collection systems, or have involved multi-chamber collection vessels with a sac or liner removably inserted in the collection chamber.

While such systems are able to collect and, in some cases, to deliver blood for reinfusion, they have various drawbacks as far as efficiency of use or optimal handling of collected blood. Thus there exists a continuing need for an improved blood recovery system.

BRIEF DESCRIPTION OF THE INVENTION

Accordingly, it is an object of the invention to provide a blood collection system of enhanced efficacy and ease of use.

This is achieved in accordance with one embodiment of the present invention by providing an internally stented isocompliant bag for interposition between a drainage site and a suction supply. Blood line quick connects at the bag allow ready removal of the bag from the system for reinfusion, and the substitution of a second vessel. In the preferred embodiment, the internal stent mechanism essentially consists of a folding and preferably transparent box-like shell, and an expansion spring mounted within the shell to urge it into an open or expanded state. The shell bears against the inner walls of a bag formed of a PVC or other blood-compatible film, which is thereby spring-loaded into a defined vessel volume and shape.

In use as a collection bag, the assembly is supplied at its inlet with a suction of about twenty centimeters of $H_2O$, thereby drawing the walls inward against the force of the internal compression spring, compressing it somewhat. This narrows a funnel shaped flex joint formed at the bottom of the stent, and induces a slight concavity of the vessel side walls, thus decreasing the vessel cross-sectional area by about twenty percent. As suction varies, due for example, to erratic conditions at the drain inlet as clotted blood is being drawn into the bag, the vessel is free to increase or decrease its volume in response to suction changes. The spring loaded walls thus modulate any abrupt increase or decrease in suction.

Preferably, no filter is provided at the upper drain tube inlet, and collected blood passes quickly and uniformly to an angled pooling region enclosed by the stent at the bottom of the bag. A gross filter, preferably a screen filter, surrounds the pooling region and has a large area and mesh size such that a normal gravitational infusion pressure head of 30-70 cm $H_2O$ is adequate to draw the collected blood from the vessel. An ergometrically-positioned injection port at the blood inlet, and an openable filtered vent are provided at the top of the bag. The face of the bag preferably has two volumetric scales printed thereon to accurately indicate the volume of blood under the two different conditions of normal suction, during collection, and atmospheric pressure, during reinfusion. Other features of the basic invention and preferred embodiments thereof will be understood from the following description, taken together with the drawings and claims, read in light of the existing art.

BRIEF DESCRIPTION OF THE DRAWINGS

FIG. 1 shows an in-line blood collection system in accordance with one embodiment of the present invention;

DETAILED DESCRIPTION

Figure 3C:
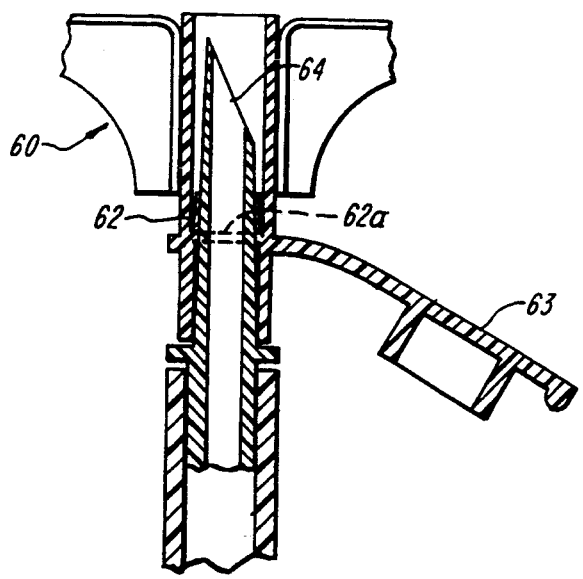
FIGS. 3A, 3B and 3C show central sections taken in a plane directed axially along the respective three ports of the bag in the positions indicated in FIG. 2.

In accordance with a basic embodiment of the present invention, a vessel 2 for the collection and reinfusion of blood attaches to a regulated suction supply vessel 1 and to a patient drain tube 3 to draw blood from a wound or surgical opening. The vessel attaches in line, via releasable fluid quick connect couplers 11, 12, as disclosed further below, and may be detached from the line to deliver its contents, via a spike port outlet 13, to the vascular system of a patient by gravity infusion.

Figure 2:
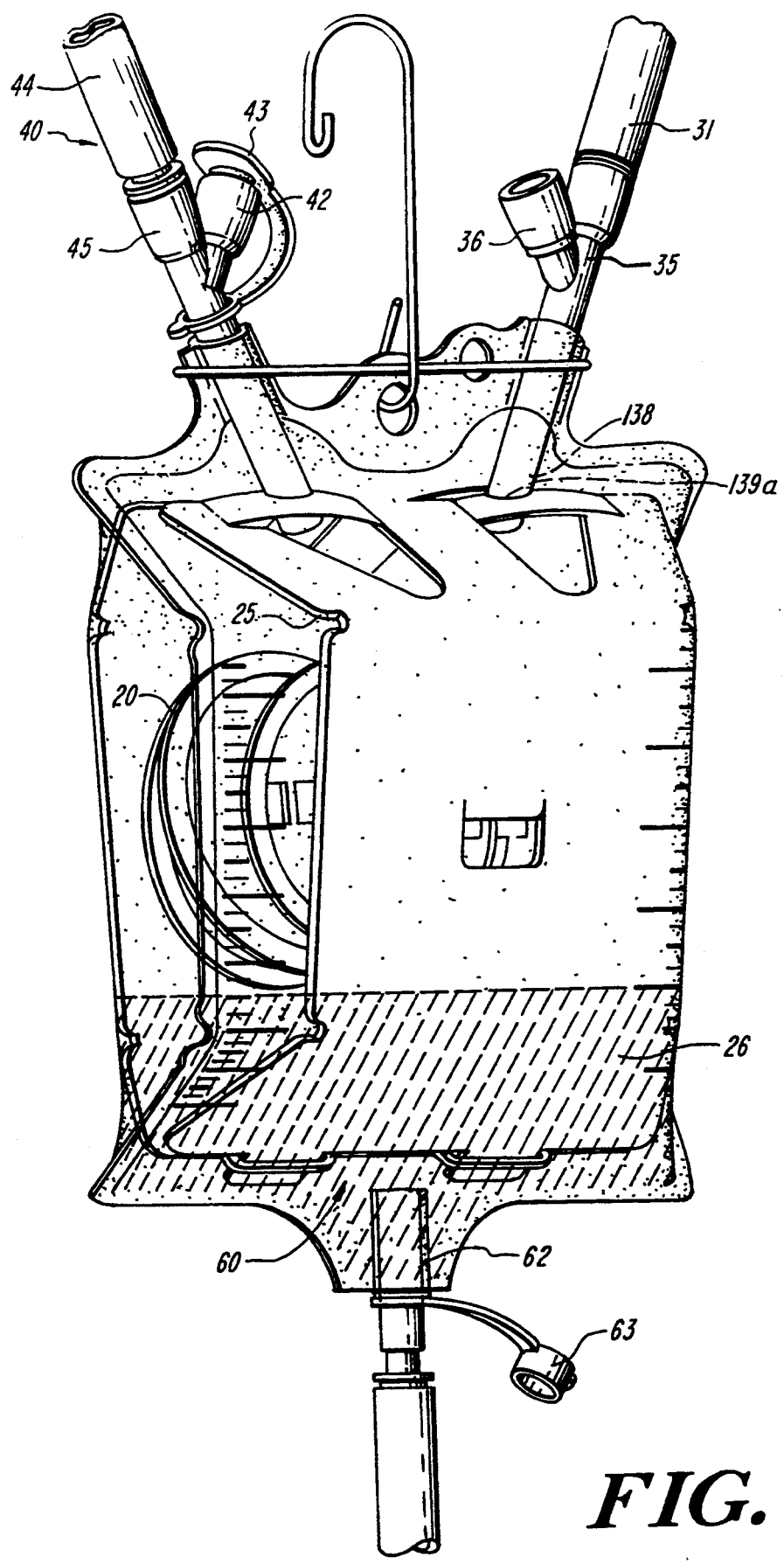
FIG. 2 is a detailed perspective view of the in-line collection vessel shown in FIG. 1.

Vessel 2 has a unique structure that enhances collection and reinfusion with minimal damage to the collected blood. In one aspect, this structure includes an internal stent structure that biases the bag walls outwardly into a box-like shape of defined volume, yet yields elastically in response to sharp variations in suction during fluid collection. The stent structure includes a compression spring 20 which urges a rigid hinged polymer or biocompatible flex frame 25 (FIG. 2) into an open box-like position. Preferably this frame is formed of a clear, transparent plastic, allowing ready visualization of blood level from any direction.

In the illustrated system employing a "wet" chest drain 1 as a suction source, that is, one preferably having a water-filled manometer structure, a water seal chamber, or both, such abrupt suction spikes often occur, for example, when clotted blood is sucked along or out of the patient drain tube 3. Suction spikes or dips may also occur from sudden kinking of a vacuum tube, or from patient spasms, under certain conditions.

The bag 2 preferably has a volume slightly greater than one standard blood unit, e.g., about 600 ml., and under conditions of no suction the internal spring 20 expands to a length of approximately five centimeters, urging the frame 25 outwardly to this extension against the bag walls. Under a suction level of approximately −100 cm $H_2O$, the atmospheric pressure on the walls compresses the spring 20 down to below four centimeters length. The flexible side walls 2a of the vessel also bow inward, thus reducing the interior volume by an amount more than proportionate to the pressure drop. At a normal level of suction for blood collection, of approximately −20 cm H₂O, all the walls retract somewhat, and with the spring thus preloaded in an intermediate position, any abrupt increase or decrease in suction causes an immediate corresponding shortening or lengthening of the spring and a concommitent volume change that effectively counteracts the change in suction. That is, in general, a rapid suction increase or spike decreases the volume, with the effect of raising the interior pressure and thus counteracting the negative suction change, while a dip or lowering of suction level (increase in pressure) relaxes the spring, increasing the interior volume with the effect of lowering the interior pressure, thus counteracting the positive pressure change. While the overall change in volume with pressure is not substantial owing to the particular shape of the bag and stent, the immediate effect for very abrupt suction changes is to modulate sharp spikes, and thus to prevent the damage to blood cells that might be caused by extreme abrupt pressure changes.

In accordance with the present invention, two sets of volumetric graduations 2b, 2c of differing scale are provided on the face of the collection bag. Scale 2b may be imprinted on side 2a, a side which normally would face the wet drain 1 owing to its connection thereto by short suction tubes. This scale shows the true volume of collected blood when no suction is applied to the bag. The second scale 2c is imprinted on the opposite side of the bag, but has level lines that "wrap-around" onto the broad front face of the bag. These lines show the volume level when the stent and bag have assumed a thinner profile upon application of −20 H₂O suction, i.e., during normal blood collection. They are visible from several sides of the bag, allowing the ready recognition of the occurrence of an excessive bleeding condition.

The connection to patient inlet line 3 is effected with a quick connect female coupler 12, described further below with reference to FIGS. 4 and 5 on a short length of large diameter thoracotomy tubing 31 extending from an inlet manifold 35 and forming an unobstructed drain path for blood flow into the bag. Unlike most conventional blood collection structures which utilize suction to draw the collected blood through a gross filter or sock filter at a vessel inlet, this flow path has no filter, and thus does not subject the blood to clogging and drying out, nor does it subject blood cells to the physical trauma of being forced through a filter under pressure.

Figure 3A:
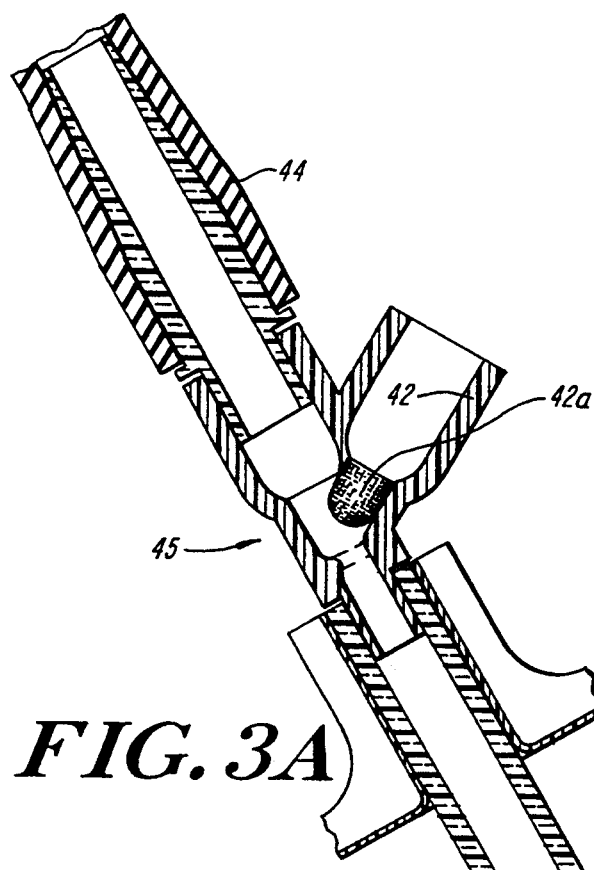
Figure 3B:
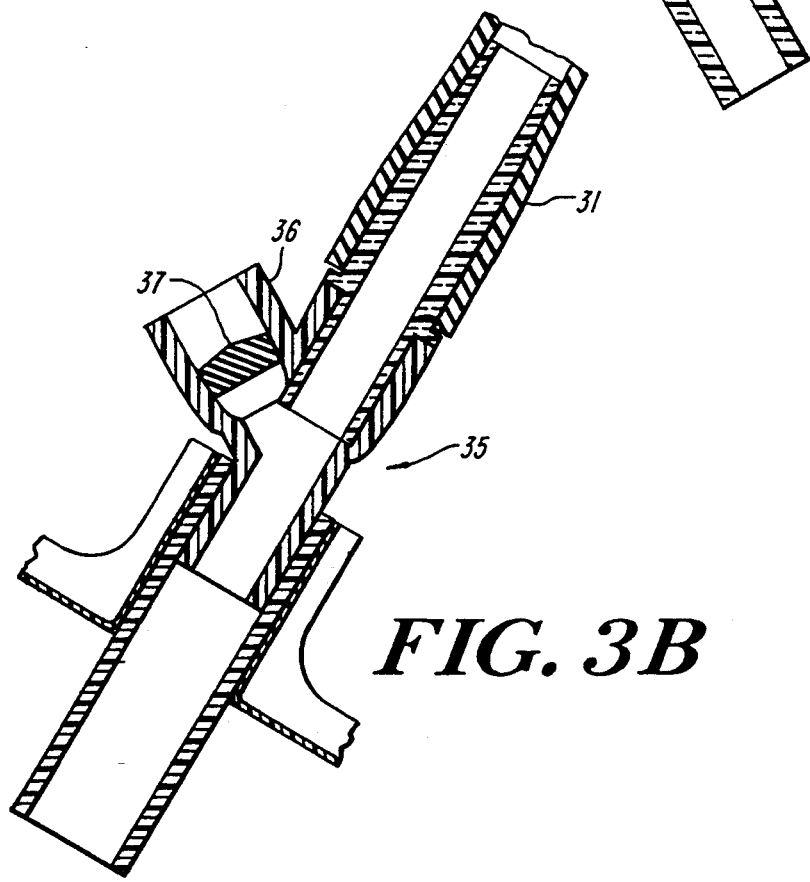
Figure 3C:
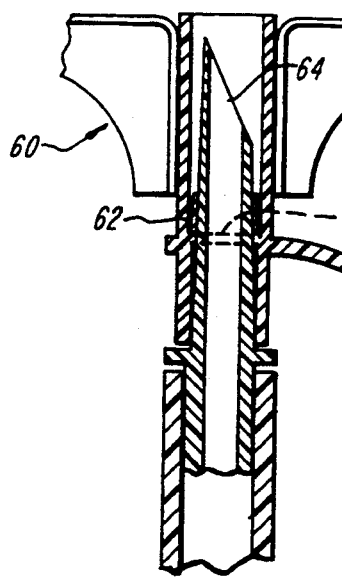
Figure 5A:
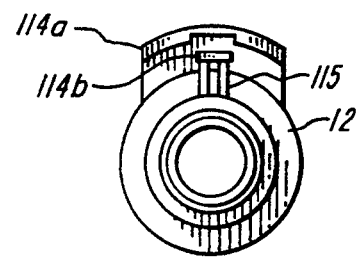
Figure 4:
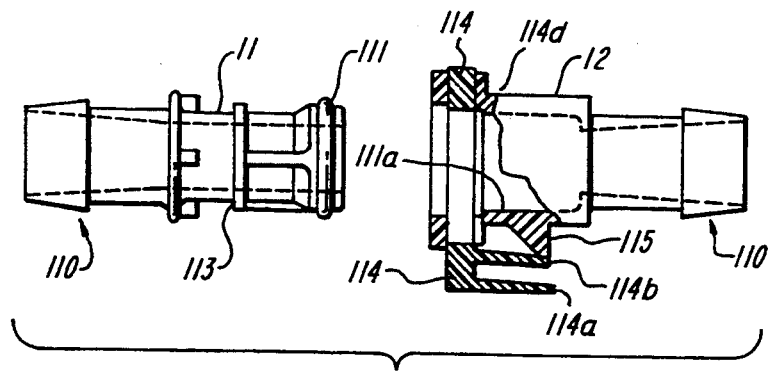
Figure 5B:
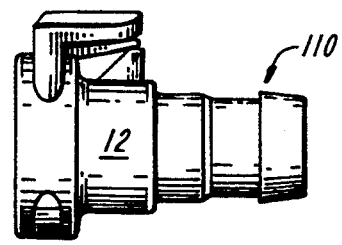
Figure 5C:
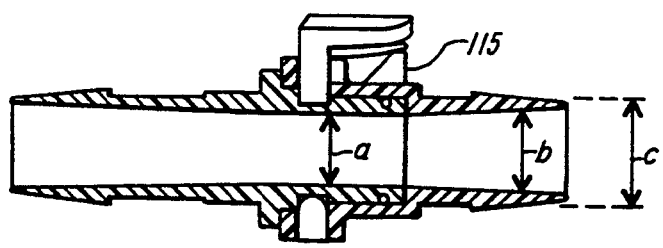

The inlet manifold 35 also includes a branch port 36, which has a pierceable self-resealing septum 37 (FIG. 3B). Branch port 36 is located such that anticoagulant injected at the septum enters the incoming fluid, and is carried by a non-occludable tubing extension 138 through a stent opening 193a below the top edge of the internal frame 25 into the bag interior. Tube 138 is a quarter inch ID tube of a type normally used in fabricating blood collection or infusion bags. The bag itself is formed of a twenty to twenty-six mil thick biocompatible PVC or similar film, which is solvent, radio frequency, or vibration welded or cemented about its edges and ports into a closed structure. Thus, the inlet blood path is an open, drop-through non-occluding path that causes minimal, if any, damage or dessication to the collected blood.

At the suction inlet 40, a symmetrically placed vent port 42 extends from the suction inlet manifold 45. A plug 43 is mounted on manifold 45 for capping or closing vent port 42 under normal collection conditions. Manifold 45 connects to the suction source or vessel 1 via a short length of anti-kink reinforced thoracotomy tube 44, terminated by a male quick connect 11 (FIG. 1). When removed from the line, connectors 11, 12 connect to each other, closing the bag against contamination and also forming a handle by which the vessel 2 may then be carried. Similarly, the mating connectors on the suction vessel and on the patient drain tube, to which the bag connectors were each previously connected, may then be directly connected to each other to allow body fluids to continue to be drawn. In this case, these subsequently collected fluids collect directly in the suction vessel 1, which may, for example, be a conventional wet chest drain unit.

At the bottom of vessel 2 a fabric screen or mesh filter 26 fits over the hinged stent 25 and around the sides to form a boat-shaped large area filter through which blood pooled in the container passes, thus constituting a relatively open filtration body in a path leading to a funnel shaped outlet region 60 of the collection vessel 2. A spike port 62 extends from the lowest point of the outlet region 60, and a cap 63 closes the spike port to maintain its sterility during collection and until attachment to an infusion line.

In use, once blood has been collected and the vessel 2 detached from the patient tube 3 and from the suction source 1 as described above, port 62 is attached to an infusion line, vent port 42 is opened and the infusion line is bled, and the collected blood may pass by gravity flow from vessel 2 for reinfusion. A bacterial filter, such as fibrous plug filter 42a, is located in the vent 42, and prevents bacteria from entering the vent port, as illustrated in FIG. 3A. Other types of filter, such as a micropore filter, may be used.

FIGS. 3A, 3B and 3C show sections, each taken in a plane passing through the central axis of each of the respective injection, vent and outlet ports. As illustrated, each of these ports has a blocking structure to assure sterility at some stage of operations, as well as a cap element that allows it to be sealed closed at relevant stages of operation.

Specifically, the injection port 37 has a pierceable self-sealing septum 37 in the form of a relatively thick plug of soft, non-coring polymeric material that self-reseals after injection; it may also have a cap (not shown) initially closed to maintain sterility of the surface of septum 37. This allows the injection of medicine or anticoagulent into the collecting blood stream, or into the collection pool during collection or infusion.

The vent port 42 located in the suction inlet manifold 45 is initially closed by cap 43 (FIG. 2) to maintain a sealed chamber that allows operation as a suction vessel. For infusion of collected fluids, however, cap 43 is removed and the plug filter 42a then allows relatively unhindered, but filtered, ingress of the surrounding air. This allows blood to be drawn from the vessel despite the fact that internal spring 20 maintains the bag expanded in a fixed volume. Thus, reinfusion does not require external mechanical devices such as a bag squeezer and/or an infusion pump.

The outlet port 62 is initially sealed by a thin diaphragm 62a, and capped by cap 63. For reinfusion, the cap is opened and a mating spike connector 64 is inserted, piercing the diaphragm 62a.

As illustrated in the perspective view of FIG. 1, the in-line vessel 2 is preferably provided with pinch clamps 71, 72 in place over the short patient inlet and suction inlet tubes 31, 44. These large, easily manipulated clamps are closed before removing a filled bag from the collection circuit. They may be closed in either order, and provided that at least one clamp is closed, the operation of detaching the vessel from the line is a neat and hygienic one. Each clamp is secured in a position of optimum accessibility by being sandwiched between a quick-connector body (11 or 12), on one side, and a large anti-kink tube shield 73, on the other side. This prevents the clamps from sliding along the suction inlet tube of the patient drain tube (which may each have their own clamp) or from shifting along the connecting tube stubs 31, 44, so they do not get lost or moved into inaccessible positions. Thus, the bag and its accessories are positioned to allow instantaneous disconnection for initiating reinfusion in an emergency.

In accordance with a further aspect of the invention, the various conduit junctions are unobstructed flow segments that do not introduce flow irregularities. In particular, the large bore thoracotomy tube interconnecting vessels 1 and 2, and connecting vessel 2 to the patient, are connected by large bore blood-compatible quick connects, described further below.

Figure 4:
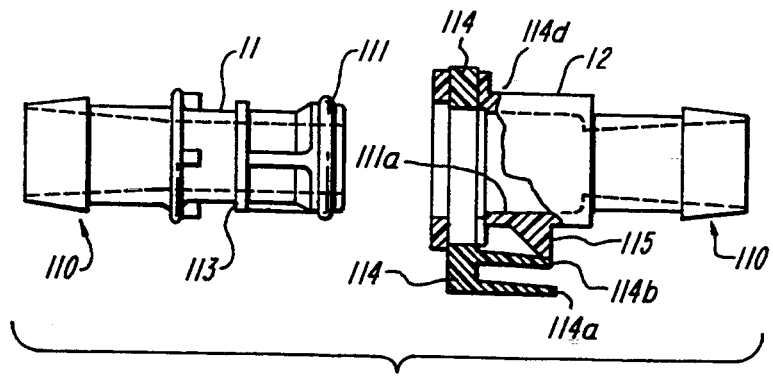
FIG. 4 illustrates a perspective view, partially cut away, of a quick connector at the inlet and outlet of the collection vessel of FIG. 2.

Quick connects 11, 12 are shown in FIG. 4, and have a basic engagement structure in common with many couplers of the prior art. Specifically, each has an external barb 110 that fits within a tube and retains the tube thereon without requiring a circumferential clamp, cement or the like. Male or plug connector 11 has a sealing O-ring 111 about its circumference that seals against inner wall 111a of the female or socket connector 12 when inserted. A protruding flange 113 of the plug connector is engaged by a spring-biased locking slide plate 114 in the socket. In this embodiment, locking slide plate 114 is a separate plastic plate that slides radially across a slot in the socket housing, and having a slot therein with small detent protrusions 114d that engage an axially oriented face of flange 113 in its relaxed position. Locking slide 114 is urged into its locking position by an integrally formed finger 114b that rests against a protruding nub 115 formed on the socket housing. When plug 11 is inserted into socket 12 flange 13 pushes against nub 114d, urging the slide plate 114 upwardly as it enters, and snapping into fluid-tight engagement. The back (inward) face of hubs 114d are not rounded, so axial pull on the tube will not induce a similar motion of the slide plate, and the connectors are separable only by pressing downward on thumb release 114a.

Figure 5A:
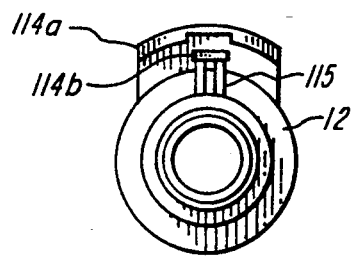
FIGS. 5A–C are elevations and sectional views of the quick connector.

FIG. 5A Shows an end view from the tubing end of the female connector 12, showing the relative thicknesses of spring finger 114b and thumb release finger 114a. Both fingers are integrally molded in the slotted lock plate 114 (FIG. 4), which is formed of acrylic, polycarbonate or similar strong moldable plastic. The connector has a clear unobstructed though passage of approximately 25/64 inch diameter, dimension "a" in FIG. 5C.

Figure 5B:
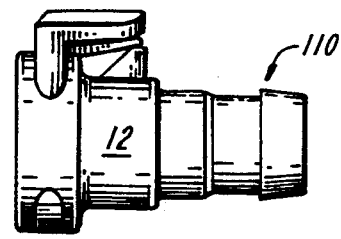
Figure 5C:
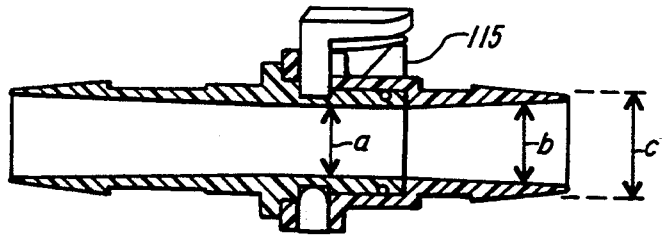

As shown in FIG. 5B, the barb end 110 tapers to a knife-edge rounded tip, and extends outwardly to a wider diameter "C" FIG. 5c of approximately 9/16 inch to secure the connector in a thoracotomy or similar-size tube. The cross-section of the connector body, shown in FIG. 5C has an inner face of gradually increasing diameter, so that the passage flares outwardly at its ends to a widened diameter "6" in FIG. 5C of about ¼ inch. This results in a wide and unobstructed flow path. In particular, the connector body presents a very thin edge at is juncture with the housing wall which is effectively flush with the tube wall and presents no obstruction to blood. It will be appreciated that these stated dimensions are adapted to present an effective coupling with minimal flow passage protrusion or obstruction when used with the aforesaid thoracotomy tubing. Other relative dimensions may be suitable for other tubing sizes or materials. Applicant further notes that the provision of identical connectors of this type on vessel 2 and on the tubes from vessel 1 and from the patient, assures that when the second vessel is removed from the line to reinfuse or dispose of its contents, the "vacuum" line from vessel 1 functions equally well as a blood-carrying patient drain line.

The modular quick connect vessel as described above will be seen to offer many useful advantages and support new methods of use that are significant in a clinical setting. For example, rather than one vessel 2 as illustrated in FIG. 1, two or more such vessels may be strung together in series. With such an arrangement, useful during surgery when massive bleeding is expected, the vessel 2 nearest the patient will fill first, at which time it may be removed to allow the next vessel to fill. Advantageously, when the first vessel has been removed, only one connection (of the patient drain line 3 to the already connected next vessel) is required to resume collection, rather than the two connections otherwise required to install a new vessel in line. The open path flow connectors allow several vessels to be used in series this way, without significant decrease in suction draw.

The invention has been described above with special reference to a presently preferred embodiment of an in-line collection vessel and associated connectors. Such description is not intended to limit the invention, but rather serves as a guide to its different features and advantages so as to enable the practice thereof. Different variations, modifications, equivalents and improvements of the described structure together with other methods of use will occur to those skilled in the art, and all such variations, modifications equivalents and improvements are considered to be within the scope of the invention, as defined by the claims appended hereto.

We claim:

1. Apparatus for the collection and reinfusion of blood comprising a blood bag formed of flexible sheet material and configured for use with a source of suction having a normal suction level and subject to occasional excessive suction, said blood bag having an unobstructed inlet for receiving a flow of blood and a substantially unobstructed suction inlet connectable to the source of suction, both inlets being located in a top region, and an outlet port located in a bottom region of the blood bag, and an internal stent enclosed within said blood bag and having a spring resiliently urging the stent outwardly against walls of the blood so that the bag forms a container of defined volume, the spring having a force constant selected so that the spring is preloaded in an intermediate position at said normal suction level and the stent moves inwardly, when said excessive suction is applied due to atmospheric pressure exerted on surrounding bag walls, resulting in a defined cross-section inside the bag that varies in use as a function of suction level, said stent moving in response to changes of suction level to vary said volume for modulating abrupt variations of suction level applied through said blood flow inlet.

2. Apparatus according to claim 1, wherein the inlet for receiving a flow of blood and the suction inlet each include a quick connect for interposing and removal of the apparatus in-line between a patient and a suction source.

3. Apparatus according to claim 2, wherein the quick connects are of opposite type to mate with each other, for sealing the inlets against contamination when the blood bag is removed from between the patient and the suction source.

4. Apparatus according to claim 3, wherein each inlets includes an inlet tube, both inlet tubes connecting to each other via said quick connects to simultaneously close the blood bag and form a tubular handle extending over the blood bag.

5. Apparatus according to claim 1, wherein the outlet port is a spike port.

6. Apparatus according claim 1, wherein at least one said inlet is part of a manifold including an additional inlet.

7. Apparatus according to claim 6, wherein the additional inlet includes at least one of a filtered air inlet and a resealable injection inlet.

8. Apparatus for the collection and reinfusion of blood comprising
a blood bag formed of flexible sheet material and having an unobstructed inlet for receiving a flow of blood and a suction inlet for connecting to a source of suction, both inlets being located in a top region wherein each inlets is part of an inlet manifold that includes an additional port, and an outlet port located in a bottom region of the blood bag, and
an internal stent enclosed within said blood bag and having a spring resiliently urging walls of the blood bag outwardly to form a container of defined volume, said stent moving in response to changes of suction level for modulating abrupt variations thereof.

9. Apparatus according to claim 1, wherein the bag is intended for operation at a defined suction level, and further comprising first and second sets of fluid level graduations thereon, said first set indicating fluid volume within the blood bag when the spring attains an intermediate length in response to said defined suction level, and said second set indicating fluid volume at atmospheric pressure when suction is no longer applied to the suction inlet.

10. Apparatus according to claim 1, wherein said stent and bag are transparent whereby blood collected therein is visible.

11. Apparatus according to claim 1, further comprising a filter forming a large area shroud surrounding a region of said stent whereby blood is filtered without substantial pressure drop and filtered blood flows by gravity flow from said outlet.

12. Apparatus according to claim 11, wherein said outlet is located at a funnel-shaped region of the bag.

13. Apparatus according to claim 1, comprising an expansion spring within the collection bag that bears against the stent so that the stent is urged outwardly by the expansion spring.

14. Apparatus for the collection and reinfusion of blood, comprising a blood bag having in a top region a substantially unobstructed suction port connectable to a source of suction for applying suction to the bag, a blood inlet port for admitting blood to the bag, said blood being drawn into the bag by suction applied at said suction port, and means for resiliently holding the bag in an open extension that varies in accordance with suction in said bag, a pair of quick connects for attaching said ports to a suction source and to a patient drain tube, respectively, and a tube extending between at least one of said suction port and said blood inlet port, and one of the quick connects, wherein the pair of quick connects are locking connectors of mating type to connect to each other thereby securely interconnecting said ports to close the bag and simultaneously the tube forms a secure handle for carrying the closed blood bag.

15. Apparatus for blood collection, comprising a flexible collection bag with a suction inlet for application of suction thereto, a fluid inlet for collection of fluid therethrough, and an outlet, and an internal stent, including a frame and a spring both located within the collection bag, that resiliently biases the bag into a fixed shape with a volume that varies with level of suction applied at the suction inlet and is less than a maximal volume when a first level of suction suitable for wound drainage is applied to said suction inlet, while changing to modulate abrupt variations in suction level as said suction level changes from said first level and further comprising a filter in the collection bag that is spread open by said stent so that collected blood passes through the filter to reach said outlet.

16. Apparatus according to claim 15, further comprising a gross filter surrounding a lower pooling region of the collection bag leading to a bag outlet port.

17. Apparatus according to claim 15, wherein the bag has plural different graduated volume scales corresponding to different suction levels acting on the bag.

18. Apparatus for blood collection, comprising a collection bag with a suction inlet, a blood inlet, and an outlet at a lower portion of the bag, a frame internally positioned in said bag about a spring to urge opposed walls of the bag away from each other to form an enclosed collection volume, and a large area filter located between the frame and the bag and maintained open by the frame for filtering blood in the collection volume as it passes downwardly to the outlet.

* * * * *